US007220978B2

(12) United States Patent
Ma et al.

(10) Patent No.: US 7,220,978 B2
(45) Date of Patent: May 22, 2007

(54) SYSTEM AND METHOD FOR DETECTING DEFECTS IN SEMICONDUCTOR WAFERS

(75) Inventors: Xianyun Ma, Lexington, SC (US); Tangali S. Sudarshan, Columbia, SC (US)

(73) Assignee: The University of South Carolina, Columbia, SC (US)

( * ) Notice: Subject to any disclaimer, the term of this patent is extended or adjusted under 35 U.S.C. 154(b) by 418 days.

(21) Appl. No.: 10/413,657

(22) Filed: Apr. 15, 2003

(65) Prior Publication Data

US 2004/0206891 A1    Oct. 21, 2004

(51) Int. Cl.
*G01N 21/88* (2006.01)
*G01N 21/86* (2006.01)
*G01N 21/00* (2006.01)
*G02F 1/01* (2006.01)
*G01J 4/00* (2006.01)

(52) U.S. Cl. .................... 250/559.45; 250/559.04; 250/225; 356/237.4; 356/364

(58) Field of Classification Search ........... 250/559.45, 250/225, 559.04, 559.05, 559.06, 559.46, 250/559.09, 559.07, 559.08; 356/237.2, 356/237.1, 30, 31, 239.1, 237.4, 237.3, 364; 348/125, 126

See application file for complete search history.

(56) References Cited

U.S. PATENT DOCUMENTS

| 5,248,876 | A  | * | 9/1993  | Kerstens et al. | ....... 250/559.05 |
| 6,825,487 | B2 | * | 11/2004 | Preece | ..................... 250/559.4 |
| 6,900,892 | B2 | * | 5/2005  | Shchegrov et al. | ......... 356/369 |
| 2003/0178588 | A1 | * | 9/2003 | Ota | ........................ 250/559.45 |
| 2004/0087112 | A1 | * | 5/2004 | Liu | .............................. 438/460 |

* cited by examiner

*Primary Examiner*—Georgia Epps
*Assistant Examiner*—Don Williams
(74) *Attorney, Agent, or Firm*—Douglas W. Kim; McNair Law Firm, P.A.

(57) ABSTRACT

A system and method for detecting defects in semiconductor wafers in a rapid non-destructive manner. Defects in semiconductor wafers can include micropipes and screw dislocations, stress striations, planer defects, polytype inclusions, and others. When a wafer is illuminated by polarized light, the defects induce birefringence of the polarized light that can be visualized by a polariscope to detect defects in wafers. Defects can cause linearly inputted polarized light to emerge as elliptically polarized light after transmission through a wafer having defects. Placing the wafer between a set of polarizers under the cross poles condition allows for a rapid non-destructive system and method for delineating and locating defects within a semiconductor wafer.

33 Claims, 3 Drawing Sheets

SYSTEM AND METHOD FOR DETECTING DEFECTS IN SEMICONDUCTOR WAFERS

FIELD OF THE INVENTION

This invention is directed to a system and method for determining defect delineation in semiconductor wafers and more specifically a non-destructive system and method for utilizing polarized light microscopy to delineate and map defects in semiconductor wafers.

BACKGROUND OF THE INVENTION

Semiconductor devices, such as diodes, transistors, and integrated circuits are found everywhere in modern society. These devices are used in automobiles, cell phones, computers, televisions, satellites, and many other products. The semiconductor market has grown at a staggering pace over the years with improvements in performance and reduction in cost measured in orders of magnitude. This drastic improvement in semiconductor technology is due to the skill and technology advances in the ability to miniaturize devices so that more complicated devices can occupy smaller footprints on a wafer. The technology for the manufacture of semiconductors, specifically silicon devices, has matured into a reproducible and reliable manufacturing process. However, the manufacturing process is not perfect and wafers are still created that contain defects. Some of these defects prevent the full area of the wafer from being used as any device located over such a defect causes the device to fail or otherwise become inoperable. When an imperfection exists on a wafer, it is advantageous to know the location and level of imperfection so that the area sufficient for placing a device on a wafer can be known. Further, by performing the automatic mapping of defects during the manufacturing process, the growth parameters can be advantageously modified for improving crystal quality in subsequent wafer growth. Once the wafers are manufactured, the invention can assist with insuring quality control by measuring defects in specific production runs.

Referring now to a specific example, silicon carbide (SiC) wafers can be used for manufacturing high-frequency, high-powered, or high-temperature operating conditions for devices. Some of the advantages of SiC devices are that they have lower power dissipation, lower current leakage, and higher operational temperatures. In creating SiC devices, a SiC wafer is used as a foundation for the device. Unfortunately, SiC wafers contain defects, including dislocations such as threading edge, screw, and basal plane dislocations, and stacking faults. Specifically, micropipes are small tubular voids in the wafer that are generally oriented normal to the polished surface. The existence of micropipes and screw dislocations in the wafer, especially in high densities, prevents the use of large device areas for more powerful and complex devices. In fact, micropipes and screw dislocations have been identified as the main obstacle for commercializing large-area power devices. Micropipes lead to premature reverse breakdown in the SiC p-n junction and clearly adversely affect the electrical performance of the SiC device. The ability to detect the existence and physical location of the micropipes and screw dislocations on a wafer allows device manufacturers to determine the physical areas of the wafer where devices can be placed so that such defects will not degrade or destroy the functionality of the device.

Previously, methods for determining the number and location of micropipes in SiC wafers include KOH etching and transmission electron microscope (TEM). However, both are destructive methods resulting in a non-usable SiC wafer and not well suited for production line testing. While other methods exist, they require expensive equipment or special facilities. For example, synchrotron white-beam x-ray topography (SWBXT) requires a synchrotron light source that is available in only a few research facilities in the world. Other methods, such as atomic force microscopy (AFM), scanning electron microscopy SEM, and optical microscopy, while detecting micropipes, cannot detect closed-core screw dislocations in a non-destructive fashion. More specifically, it is advantageous to delineate and locate defects of the epitaxial films or layers. It is known that threading defects, such as micropipes, threading edge and screw dislocations, and grain boundaries, originating in the SiC or other substrate, penetrate the device structure during epitaxial growth and cause device failure or other inoperability. Further, process induced morphological defects can be caused by processes such as cutting, polishing, and preparing a wafer for growth.

Previously, there has not been an effective method or system to characterize the crystallographic defects and resulting morphological defects in the epilayer. Further, there has not been previously an effective method or system to determining threading defects, their propagation, or their correlation with growth pits of the epilayer, with or without the epilayer present.

Therefore, the development of a non-destructive, inexpensive, and rapid detection system and method for determining defects in semiconductors is a problem to which much attention should be directed.

Accordingly, it is an object of this invention to provide for an inexpensive, rapid, non-destructive system and method for determining defects in wafers.

It is another object of this invention to provide for an inexpensive non-destructive system and method for determining defects in wafers, with or without an epilayer.

It is another object of this invention to provide for an inexpensive non-destructive system and method for investigating threading defect propagation.

It is another object of this invention to provide for an inexpensive non-destructive system and method for investigating the relationship between wafer defects and device performance.

SUMMARY OF THE INVENTION

The above objectives are achieved according to this invention by utilizing a polarized light microscope for performing a rapid, inexpensive, and non-destructive defect delineation of defects including micropipes, stressed striations, inclusions, dislocations, and grain boundaries. This invention can easily determine the location and therefore map defects of wafers including expitoxial films such as SiC, GaN, AlN and AlGaN. The invention provides for A system for delineating defects in a semiconductor wafer comprising a computer readable medium in communications with a CCD and a display monitor, an analyzer disposed adjacent to the CCD for analyzing polarized light received by the CCD and transmitted through the semiconductor wafer, a polarized light source for transmitting light through the semiconductor wafer so that the CCD can receive image information representing defects illuminated by the polarized light; and, a set of computer readable instructions included within the computer readable medium for allocating a plurality of scan regions associated with the semiconductor wafer, receiving scan information representing at least one scan region from the CCD, and displaying the scan information on the display monitor so that defects of the semiconductor wafer illuminated by the polarized light may be rapidly determined in a non-destructive manner. The system can also contain computer readable instructions for storing the scan information within the computer readable medium, cumulating the scan information to create a digital map representing the entire area of the semiconductor wafer and displaying the digital map. A movable scanning plate can be included, having an actuator, in communications with the computer readable medium; and, the set of computer readable instructions include instructions for receiving wafer placement information representing the location of the wafer on the scanning plate, actuating the scanning plate according to the wafer placement information so that scan information is received by the CCD for at least one of the plurality of scan regions associated with the semiconductor wafer. The invention can also contain an actuator for actuating the CCD in communications with the computer readable medium; and, the set of computer readable instructions include instructions for receiving wafer placement information representing the location of the wafer on the scanning plate, actuating the CCD according to the wafer placement information so that scan information is received by the CCD for at least one of the plurality of scan region associated with the semiconductor wafer. The invention can also contain a reflective light source disposed adjacent to the scanning plate for reflecting light off the wafer to be received by the CCD and, the computer readable instructions include instructions for receiving reflective light information reflected off the wafer and displaying the reflective light information on the display monitor so that distortions in the reflective light, representing defects in the wafer, can be viewed. A set of defect characteristics contained in the computer readable medium and the set of computer readable instructions include instructions for reviewing the scan information, determining the existence of defects by identifying defects according to the defect characteristics in the scan information so that a system to automatically locate defects in the semiconductor wafer is provided. The invention can contain computer readable instructions for determining areas of contrast differentiation representing the wafer edge according to the scan information, creating boundary information according to the areas of contrast differentiation, and calculating the area of the wafer according to the boundary information.

The invention is also a method of delineating defects in a semiconductor wafer comprising the steps of providing a semiconductor, placing the semiconductor between a polarized light source and an analyzer; segmenting the semiconductor into a plurality of scan regions; and, viewing at least one scan region according to the analyzer to provide scan information for at least one scan region so that a nondestructive method for determining defects in the semiconductor wafer using polarized light is provided. The steps of displaying the scan information so that any defects in the semiconductor wafer can be viewed, storing the scan information for subsequent review, viewing a plurality of scan regions for providing a plurality of scan information; and, cumulating the plurality of scan information from the scan region so that a map having a plurality of scan information for a plurality of scan regions is provided can also be included. The steps of displaying the map having the plurality of scan information, providing a set of defect characteristics and, reviewing the scan information for determining the existence of defects by identifying defects according to the set of defect characteristics shown in the scan information can also be included. The steps of reflecting reflective light off the semiconductor wafer; and, viewing the reflective light so that distortions created by defects within the semiconductor wafer can be seen representing defects within the semiconductor wafer, determining areas of contrast differentiation representing the wafer edge according to the scan information, creating boundary information according to the areas of contrast differentiation representing the boundaries of the semiconductor wafer, and calculating the area of the wafer according to the boundary information can also be included.

DETAILED DESCRIPTION OF THE INVENTION

Figure 1:
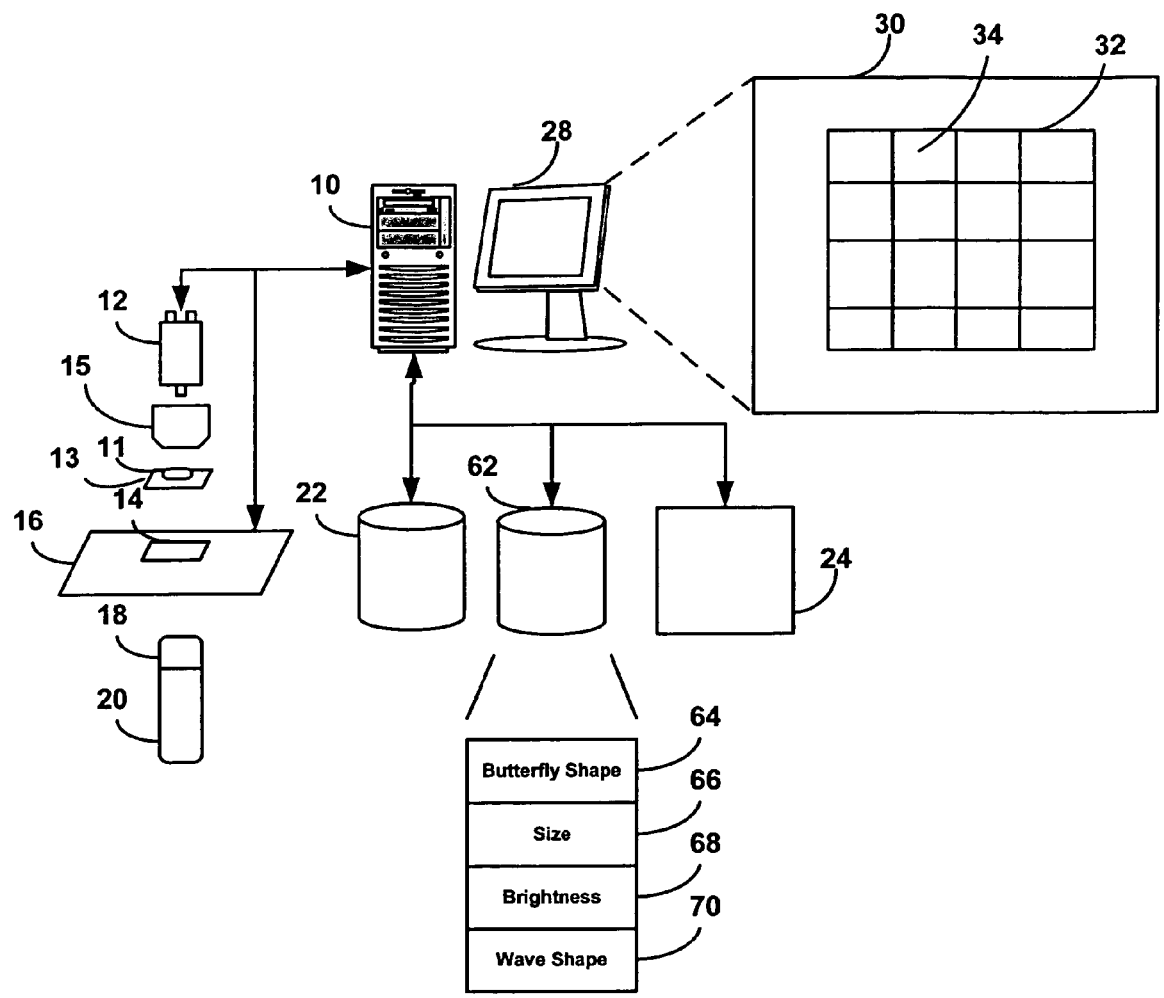
FIG. 1 is a schematic of the invention.

The detailed description that follows may be presented in terms of program procedures executed on a computer or network of computers. These procedural descriptions are representations used by those skilled in the art to most effectively convey the substance of their work to others skilled in the art. These procedures herein described are generally a self-consistent sequence of steps leading to a desired result. These steps require physical manipulations of physical quantities such as electrical or magnetic signals capable of being stored, transferred, combined, compared, or otherwise manipulated computer readable medium that is designed to perform a specific task or tasks. Actual computer or executable code or computer readable code may not be contained within one file or one storage medium but may span several computers or storage mediums. The term "host" and "server" may be hardware, software, or combination of hardware and software that provides the functionality described herein.

The present invention is described below with reference to flowchart illustrations of methods, apparatus ("systems") and computer program products according to the invention. It will be understood that each block of a flowchart illustration can be implemented by a set of computer readable instructions or code. These computer readable instructions may be loaded onto a general purpose computer, special purpose computer, or other programmable data processing apparatus to produce a machine such that the instructions will execute on a computer or other data processing apparatus to create a means for implementing the functions specified in the flowchart block or blocks.

These computer readable instructions may also be stored in a computer readable medium that can direct a computer or other programmable data processing apparatus to function in a particular manner, such that the instructions stored in a computer readable medium produce an article of manufacture including instruction means that implement the functions specified in the flowchart block or blocks. Computer program instructions may also be loaded onto a computer or other programmable apparatus to produce a computer executed process such that the instructions are executed on the computer or other programmable apparatus provide steps for implementing the functions specified in the flowchart block or blocks. Accordingly, elements of the flowchart and schematics support combinations of means for performing the special functions, combination of steps for performing the specified functions and program instruction means for performing the specified functions. The present invention is now described more fully herein with reference to the drawings in which the preferred embodiment of the invention is shown. This invention may, however, be embodied any many different forms and should not be construed as limited to the embodiment set forth herein. Rather, these embodiments are provided so that this disclosure will be thorough and complete and will fully convey the scope of the invention to those skilled in the art.

Referring now to FIG. 1, the invention is described in further detail. Computer 10 is shown connected to a digital imaging apparatus such as a charged-coupled device (CCD) 12, which can include a microscope or other magnification means, to provide for digital images derived from scanning plate 16. The scanning plate can be operatively associated with computer 10 so that the scanning plate is articulated to provide movement of wafer 14 placed on plate 16 allowing CCD 12 to scan the entire surface of wafer 14. Reflective light source 15 can be disposed adjacent to the scanning plate and can provide a light source allowing the CCD to capture images from the wafer. The computer can be informed of the physical location of the wafer on the plate and scan the wafer according to the wafer location information to insure the entire surface of the wafer is scanned. Further, the wafer can be segmented into scan regions so that the CCD captures information for each scan region and sends the captured information to the computer for storage and cumulation. By cumulating the digital information for each scan region, defects for the entire wafer can be displayed.

In order to detect the defect of a wafer, this invention uses photoelasticity since the defects of the wafer induce a change in the stress distribution around the defects location and such change can be detected to determine the location of the defect. To detect defects, light source 20, polarized through polarizing plate 18, is transmitted through wafer 14 and the optical stress is detected by CCD 12, using analyzer 13. The scan information from CCD is transmitted to computer 10. Therefore, the wafer is placed between the polarizers in the crossed poles condition. The defects of the wafer induces a stress around the defect location that is captured by the CCD. Further, the brightness of the defects as shown on the monitor corresponds to the defect distribution across the wafer. The CCD can scan a specific region or the entire wafer and collect and store the various scan regions in a database 22. Computer readable medium 24 can contain instructions for controlling the scanning plate 16, CCD 12, and for detecting defects from the information gathered from the CCD. In its operation, the wafer can be scanned, in regions or otherwise, an example of which shown as 34, then displayed on monitor 28 as image 30. Within image 30, an image of the wafer 32 is shown with various regions such as 34. The computer readable instructions allow for the magnification of the wafer, and any defects, for ease of viewing.

In one embodiment, reflective light can also be utilized in this invention. In lower quality wafers, the density of the micropipes may be too great to allow for the delineation of each micropipe as the results of the illumination from polarized light may overlap. Therefore, the intensity of the polarized light can be reduced or eliminated so as to reduce or prevent such overlap. Reflective light is then reflected off the wafer and used to delineate the micropipe, and screw defects, when used in conjunction with the polarized light. Reflective light causes a darkened area to exist with the butterfly shape so as to assist in further delineating the micropipe. Reflective light source II is disposed adjacent to scanning plate 16 so that light is reflected from reflective light source II onto wafer 14 and received by CCD 12. Distortions of the reflective light are caused by defects in the wafer, especially the epitaxial layer, and recorded by the CCD. Therefore, the defects can be identified through distortions of the reflective light.

A set of defect characteristics 62 can be contained with the computer readable medium so that the scan information can be compared to the set of defects characteristics so that the defects of the wafer can be identified. The set of defect characteristics can include information representing the butterfly shape 64, the size of the butterfly shape, or other defect 66, and the brightness 68. Further, a wave shape 70 can be included representing screw dislocations within the wafer. The wave shape is further illustrating as generally 61 of FIG. 3.

In providing polarized light, two types of polarizers could be used. First, a plane polariscope can be used for linear polarization of the light source transmitted through the wafer and received by the analyzer which results are recorded by the CCD. Second, a circular polariscope can be used with the addition of quarter wave plates on either side of the wafer and inside the space defined within the polarizer and analyzer. Using either polariscope, the defects are detected as the stressed areas (defects) of the wafer, an optically isotropic material, become anisotropic thereby showing double refraction which can be detected and captured through a CCD. The defects induce stress around the defect that is thereby detected.

Figure 2:
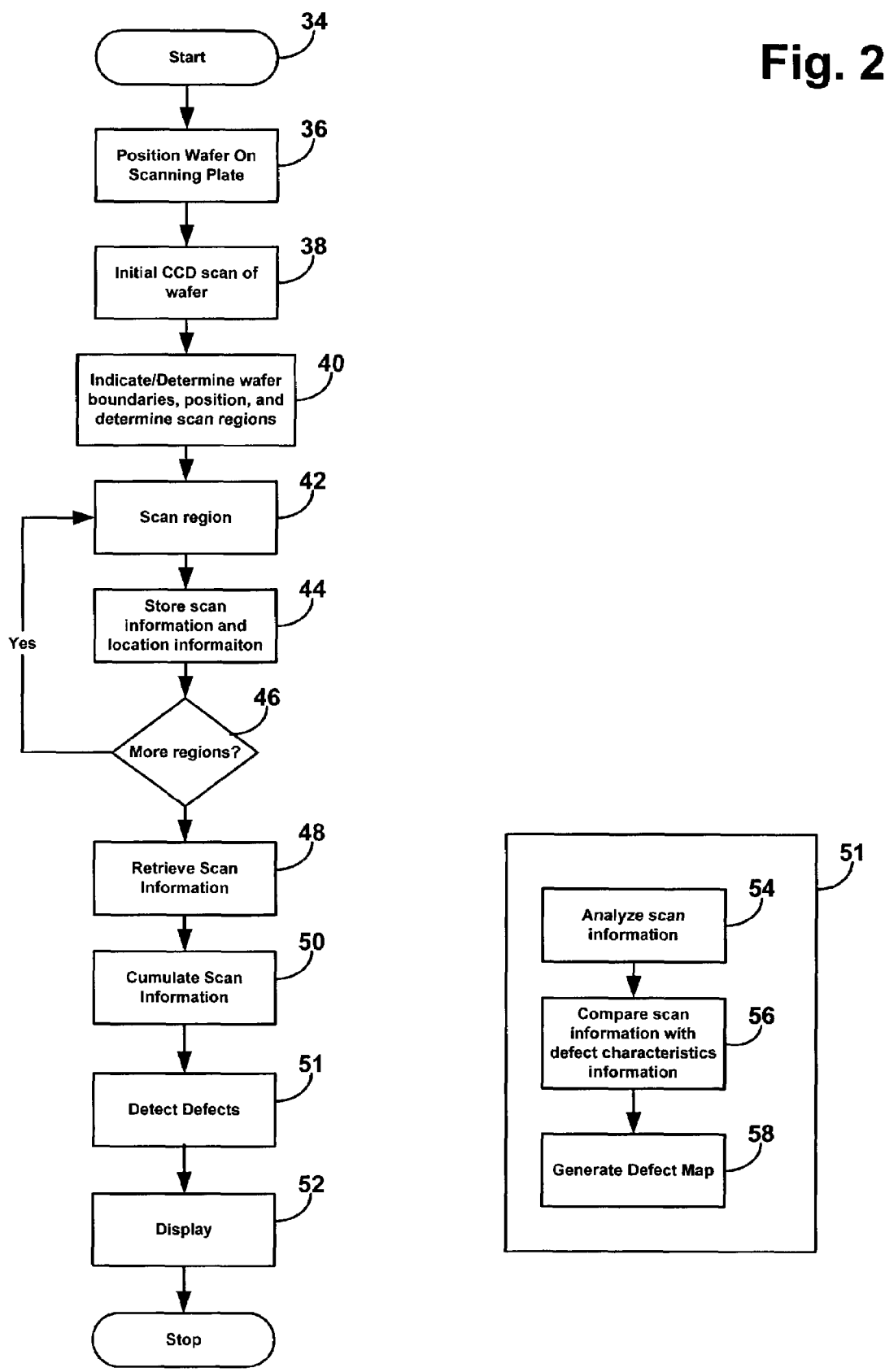
FIG. 2 is a flowchart of the invention.

Referring now to FIG. 2, the operation of this invention is shown in more detail. The process for detecting defects of a wafer begins with step 34. The wafer is placed upon the scanning bed in step 36. Providing the location of wafer 14 on scanning bed 16 begins by scanning the wafer at step 38. The image resulting from the scan is displayed on monitor 28. The boundaries of the wafer are then indicated at step 40 so that the computer readable instructions can associate the indicated onscreen boundaries of the wafer with the physical location of the CCD so that the scanning plate boundaries are known for scanning. This allows the computer readable instructions to "learn" the boundaries of the wafer so that the entire wafer can be scanned by manipulating the scanning plate. The computer readable instructions include instructions for being able to determine the wafer size from the scan information rather than relying upon the measurements of the wafer manufacturer or manual input. The boundaries of the wafer can also be determined by detecting the contrast differentiation in the light received by the CCD representing the scanning plate and wafer. Where there is a sufficient contract differentiation, there is a boundary of the wafer. Determining the boundary information allows for the wafer area to be calculated. Alternatively, the wafer could be static with the CCD itself manipulated to scan the entire surface of the wafer or the CCD of such high resolution that the entire wafer can be scanned without manipulation of the scanning plate or CCD. The scanning begins by scanning the present scan region at step 42 and the results from the scan stored in a computer readable medium, with location information, at step 44. By storing the results from each scan, the scanning process can be halted mid-process and resumed without the need to restart the scanning process. The determination of whether there are more regions to scan is made at step 46 and if so, the process returns to step 42 to scan the next region. If the determination is made that all regions have been scanned, then the scanning information can be retrieved from the computer readable medium at step 48, cumulated to form a map representing the image of the wafer at step 50, and display the map at step 52 so that the defects discovered can be seen. Through these steps, wafer defects can be magnified to tens of hundreds of micrometers in dimensions thereby allowing the location and mapping of defects to be more easily performed. Further, using color imaging technics for corresponding optical stress behavior derived from wafer defects, the nonuniformity of the wafer can be illustrated in an inexpensive, rapid, non-destructive manner. Traditional defect detection techniques simply did not allow for such location determination and mapping.

Further, the computer readable instructions can also automatically detect defects in the wafer at step 51 for display. When automatically detecting defects, the computer readable instructions can scan the digital image information cumulated from the scan information step 54 and compare the information with defect information at step 56 to provide a defect map of the defect locations on the wafer at step 58. Defect information can include the appearance of micropipes in the commonly known butterfly shape that can be detected in the digital image by comparing the digital image information with defect characteristics information to see if the pattern in the digital image corresponds to a micropipe on the wafer. More specifically, the defect information concerning micropipes can represent the butterfly shape, the size of the butterfly shape, and brightness of the illuminated defect. Based upon predetermined values for size and brightness, the computer readable instructions can compare the scan information with the existence of the butterfly shape, a predetermined size and a predetermined brightness to determine if a micropipe is present. Further, the defect information can contain a wave shape pattern that can be compared to the scan information. When the wave shaped pattern is determined to exist in the scan information, a closed core screw dislocation is known to be present.

Figure 3:
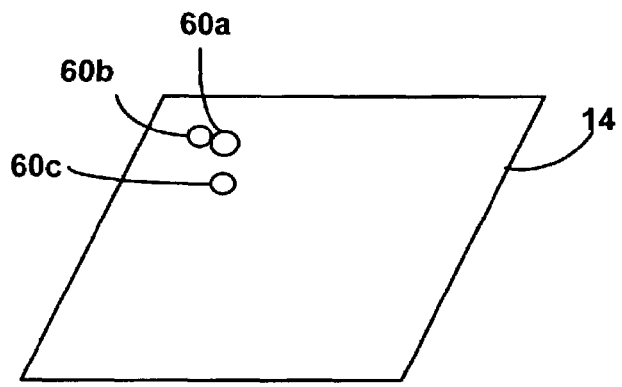
FIG. 3 is a schematic of the results of the invention.
Figure 3:
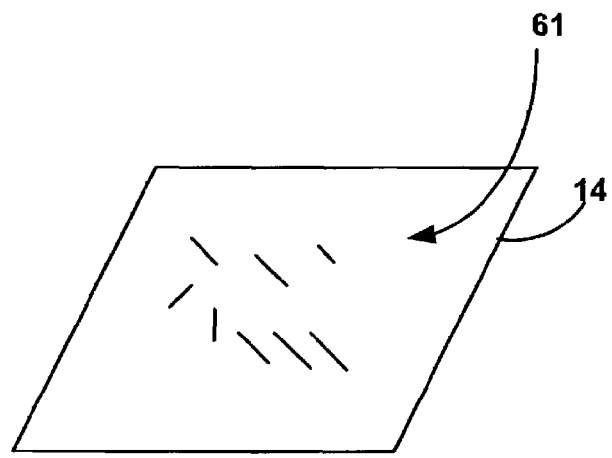

Referring now to FIG. 3, the results from this invention can be seen in further detail. The results of the invention are illustrated by showing, through the photoelasticity utilization of the invention described herein, that micropipes are located at 60*a* through 60*c* of wafer 14 and any device placed over this region would experience integrity problems. By providing such a map, the defect type, density, and location can be discovered so that the quality of the wafer and potential locations for devices can be known.

It should be understood that the detection of micropipes and screw dislocations are not the only defects that can be detected by this invention. Detection can also be made for domain boundaries, stress striation, dislocation walls, polytype inclusions, planar defects and other such defects. Further the results obtained, available in under 30 minutes from this invention, have been compared with results obtained by SWBXT and an almost one-to-one micropipe and screw dislocation matching between the results of the two analyses was shown.

It should also be known that this invention need not be limited to SiC wafers, but can also be used for other semiconductor materials and compound semiconductors including GaAS, InP, GaN, AlN, and AlGaN. Further, this invention can specifically delineate defects of wafers of substrates, even when the substrate is already covered with the epitaxial film, since a unique feature of this invention is that it can characterize a SiC wafer with or without an epilayer. Therefore, this invention provides the opportunity to determine threading defect propagation and the correlation with growth pits in the epilayer. This invention allows for the relationship between the threading defects and growth pits in the epilayer to be established. Since this invention allows for viewing micropipes, screw dislocations, stress striations, and dislocation walls that propagate through the substrate to the epilayer and open various growth pits in the epilayer surface.

While a preferred embodiment of the invention has been described using specific terms, such description is for illustrative purposes only, and it is to be understood that changes and variations may be made without departing from the spirit or scope of the following claims.

What is claimed is:

1. A system for delineating defects in a semiconductor wafer comprising:
    a computer readable medium in communications with a CCD and a display monitor;
    an analyzer disposed adjacent to said CCD for analyzing polarized light received by said CCD and transmitted through said semiconductor wafer;
    a polarized light source for transmitting light through said semiconductor wafer so that said CCD can receive image information representing defects illuminated by said polarized light; and,
    a set of computer readable instructions included within said computer readable medium for allocating a plurality of scan regions associated with said semiconductor wafer, receiving scan information representing at least one scan region from said CCD, and displaying said scan information on said display monitor so that penetrating defects of said semiconductor wafer illuminated by said polarized light may be rapidly determined in a non-destructive manner.

2. The system of claim 1 wherein said computer readable instructions include instructions for storing said scan information within said computer readable medium.

3. The system of claim 1 wherein said computer readable instructions include instructions for cumulating said scan information to create a digital map representing the entire area of said semiconductor wafer and displaying said digital map.

4. The system of claim 3 including:
    a movable scanning plate, having an actuator, in communications with said computer readable medium; and,
    said set of computer readable instructions include instructions for receiving wafer placement information representing the location of said wafer on said scanning plate, actuating said scanning plate according to said wafer placement information so that scan information is received by said CCD for at least one of said plurality of scan regions associated with said semiconductor wafer.

5. The system of claim 4 including:
    a reflective light source disposed adjacent to said scanning plate for reflecting light off said wafer to be received by said CCD; and,
    said computer readable instructions include instructions for receiving reflective light information reflected off said wafer and displaying said reflective light information on said display monitor so that distortions in said reflective light, representing defects in said wafer, can be viewed.

6. The system of claim 3 including:
    an actuator for actuating said CCD in communications with said computer readable medium; and,
    said set of computer readable instructions include instructions for receiving wafer placement information representing the location of said wafer on said scanning plate, actuating said CCD according to said wafer placement information so that scan information is received by said CCD for at least one of said plurality of scan region associated with said semiconductor wafer.

7. The system of claim 1 wherein said computer readable instructions include instructions for actuating said CCD to capture scan information.

8. The system of claim 1 including:
a set of defect characteristics contained in said computer readable medium; and,
said set of computer readable instructions include instructions for reviewing said scan information, determining the existence of defects by identifying defects according to said defect characteristics in said scan information so that a system to automatically locate defects in said semiconductor wafer is provided.

9. The system of claim 1 wherein said set of computer readable instructions include instructions for determining areas of contrast differentiation representing the wafer edge according to said scan information, creating boundary information according to said areas of contrast differentiation, and calculating the area of said wafer according to said boundary information.

10. The system of claim 1 including:
a scanning plate disposed adjacent to said CCD for supporting said semiconductor wafer to be scanned by said CCD;
a reflective light source disposed adjacent to said scanning plate for reflecting light off said semiconductor wafer to be received by said CCD; and,
said set of computer readable instructions includes instructions for allocating a plurality of scan regions associated with said semiconductor wafer, receiving reflective light information representing at least one scan region for said CCD, and displaying said reflective light information on said display monitor so that distortions of said reflective light caused by surface defects within said semiconductor wafer are visible.

11. The system of claim 10 wherein said computer readable instructions include instructions for cumulating said reflective light information to create a digital map representing the entire area of said semiconductor and displaying said digital map.

12. The system of claim 10 including;
a set of defect characteristics representing potential defects with said semiconductor wafer; and,
said computer readable instructions including instructions for reviewing said reflective light information and determining the existence of defects by identifying defects according to said set of defect characteristics located in said reflective light information.

13. The system of claim 1 wherein said polarized light source radiates cross polarized light.

14. The systems of claim 1 wherein said polarized light source radiates circularly polarized light.

15. The method of delineating defects in a semiconductor wafer comprising the steps of:
providing a semiconductor wafer;
placing said semiconductor wafer between a polarized light source and an analyzer; and segmenting said semiconductor wafer into a plurality of scan regions; and,
viewing at least one scan region according to said analyzer to provide scan information for at least one scan region so that a non-destructive method for determining defects in said semiconductor wafer using polarized light is provided.

16. The method of claim 15 including the step of displaying said scan information so that any defects in said semiconductor wafer can be viewed.

17. The method of claim 15 including the steps of storing said scan information for subsequent review.

18. The method of claim 15 including the steps of:
viewing a plurality of scan regions for providing a plurality of scan information; and,
cumulating said plurality of scan information from said scan region so that a map having a plurality of scan information for a plurality of scan regions is provided.

19. The method of claim 18 including the step of displaying said map having said plurality of scan information.

20. The method of claim 15 including the steps of:
providing a set of defect characteristics; and,
reviewing said scan information for determining the existence of defects by identifying defects according to said set of defect characteristics shown in said scan information.

21. The method of claim 15 including the steps of:
reflecting reflective light off said semiconductor wafer; and,
viewing said reflective light so that distortions created by defects within said semiconductor wafer can be seen representing defects within said semiconductor wafer.

22. The method of claim 15 including the steps of:
determining areas of contrast differentiation representing the wafer edge according to said scan information; and,
creating boundary information according to said areas of contrast differentiation representing the boundaries of said semiconductor wafer.

23. The method of claim 22 including the step of calculating the area of said wafer according to said boundary information.

24. The method of claim 15 wherein said polarized light source radiates cross polarized light.

25. The method of claim 15 wherein said polarized light source radiates circularly polarized light.

26. A system for delineating defects in a semiconductor wafer comprising:
a computer readable medium in communication with a CCD for receiving polarized light transmitted through said semiconductor wafer;
a scanning plate for supporting said semiconductor wafer disposed adjacent to said CCD;
a polarized light source disposed adjacent to said plate for transmitting polarized light through said semiconductor wafer to be received by said CCD;
a set of computer readable instructions embodied within said computer readable medium for receiving wafer placement information representing physical boundaries of said semiconductor wafer and placement of said semiconductor wafer on said plate, determining a plurality of scan regions according to said wafer placement information, directing said CCD to capture scan information representing at least one scan region, and displaying said scan information to determine the existence and location of any penetrating defects in said semiconductor wafer so that defects within said semiconductor wafer are viewable.

27. The system of claim 26 wherein said computer readable instructions include instructions for storing said scan information within said computer readable medium.

28. The system of claim 26 wherein said computer readable instructions include instructions for directing said CCD to capture map information representing a plurality of scan regions and creating a map according to said map information representing the location of defects of said semiconductor wafer.

29. The system of claim 26 including:
- a set of defect characteristics representing potential defects contained within said semiconductor wafer; and,
- said computer readable instructions include instructions for analyzing said scan information, determining whether defects exist according to said set of defect characteristics, and generating a map representing the type and location of defects on said semiconductor wafer according to said scan information.

30. The system of claim 26 including:
- a reflective light source disposed adjacent to said scanning plate for reflecting light off said semiconductor wafer to be received by said CCD; and,
- said computer readable instructions include instructions for receiving reflective light information reflected off said wafer and displaying said reflective light information so that distortions in said reflective light, representing defects within said wafer are viewable.

31. The system of claim 26 including:

a set of defect characteristics contained within said computer readable medium; and, said set of computer readable instructions include instructions for reviewing said scan information for determining the existence of defects by identifying defects according to said defect characteristics to automatically locate defects in said semiconductor wafer.

32. The system of claim 26 wherein said polarized light source radiates cross polarized light.

33. The system of claim 26 wherein said polarized light source radiates circularly polarized light.

* * * * *

UNITED STATES PATENT AND TRADEMARK OFFICE
CERTIFICATE OF CORRECTION

| | | |
|---|---|---|
| PATENT NO. | : 7,220,978 B2 | Page 1 of 1 |
| APPLICATION NO. | : 10/413657 | |
| DATED | : May 22, 2007 | |
| INVENTOR(S) | : Xianyun Ma and Tangali S. Sudarshan | |

It is certified that error appears in the above-identified patent and that said Letters Patent is hereby corrected as shown below:

Column 1, line 4, after the Title and before the Field of the Invention should read:

--FEDERALLY SPONSORED RESEARCH

This invention was made with government support under N00014-00-1-0563 awarded by the Office of Naval Research. The government has certain rights in the invention.--

Signed and Sealed this
Twenty-fifth Day of January, 2011

David J. Kappos
*Director of the United States Patent and Trademark Office*